United States Patent
Liu et al.

(10) Patent No.: US 11,133,116 B2
(45) Date of Patent: Sep. 28, 2021

(54) RADIOACTIVE SOURCE REMOVING AND INTRODUCING TOOLING, SMART CART AND SOURCE REMOVING AND INTRODUCING SYSTEM

(71) Applicant: OUR UNITED CORPORATION, Shaanxi (CN)

(72) Inventors: Haifeng Liu, Shaanxi (CN); Shiqun Xiao, Shaanxi (CN); Qi Gao, Shaanxi (CN)

(73) Assignee: OUR UNITED CORPORATION

( * ) Notice: Subject to any disclaimer, the term of this patent is extended or adjusted under 35 U.S.C. 154(b) by 65 days.

(21) Appl. No.: 16/605,632

(22) PCT Filed: Apr. 17, 2017

(86) PCT No.: PCT/CN2017/080818
§ 371 (c)(1),
(2) Date: Oct. 16, 2019

(87) PCT Pub. No.: WO2018/191852
PCT Pub. Date: Oct. 25, 2018

(65) Prior Publication Data
US 2020/0126682 A1    Apr. 23, 2020

(51) Int. Cl.
*G21F 7/00* (2006.01)
*G21F 5/12* (2006.01)
(Continued)

(52) U.S. Cl.
CPC .............. *G21F 7/005* (2013.01); *G21F 5/12* (2013.01); *G21F 5/14* (2013.01)

(58) Field of Classification Search
CPC .............. G21F 7/005; G21F 5/12; G21F 5/14
(Continued)

(56) References Cited

U.S. PATENT DOCUMENTS

| 4,664,872 A | * | 5/1987 | Kiewitz | ................ G21C 19/20 |
|---|---|---|---|---|
| | | | | 376/260 |
| 2003/0194042 A1 | | 10/2003 | Singh et al. | .................. 376/261 |

(Continued)

FOREIGN PATENT DOCUMENTS

| CN | 102693770 A | 9/2012 |
|---|---|---|
| CN | 104485144 A | 4/2015 |

OTHER PUBLICATIONS

International Search Report dated Dec. 22, 2017 in corresponding PCT International Application No. PCT/CN2017/080818.
(Continued)

*Primary Examiner* — Nicole M Ippolito
(74) *Attorney, Agent, or Firm* — Ostrolenk Faber LLP

(57) ABSTRACT

A radioactive source removing and introducing tooling includes a first support frame, a shield door disposed on the first support frame, a shield cover located on the shield door, and a first pull rod device. The shield door includes a movable first shield block. The shield cover is able to be separated from the shield door, and the shield cover includes one opening and one accommodation space. The first pull rod device includes a pull rod and a first connection portion disposed on the pull rod, and the pull rod is able to extend into the shield cover and drive the first connection portion to move inside the accommodation space of the shield cover.

18 Claims, 5 Drawing Sheets

(51) Int. Cl.
*G21F 5/14* (2006.01)
*G21F 7/005* (2006.01)

(58) Field of Classification Search
USPC ......... 250/505.1, 506.1, 507.1, 517.1, 518.1, 250/519.1
See application file for complete search history.

(56) References Cited

U.S. PATENT DOCUMENTS

| 2009/0149689 A1 | 6/2009 | Crawford et al. ................ 588/3 |
| 2014/0070118 A1 | 3/2014 | Agace ........................ 250/507.1 |

OTHER PUBLICATIONS

Written Opinion dated Dec. 22 2017 in corresponding PCT International Application No. PCT/CN2017/080818.

* cited by examiner

RADIOACTIVE SOURCE REMOVING AND INTRODUCING TOOLING, SMART CART AND SOURCE REMOVING AND INTRODUCING SYSTEM

CROSS-REFERENCE TO RELATED APPLICATION

This application is a national phase entry under 35 USC 371 of International Patent Application No. PCT/CN2017/080818 filed on 17 Apr. 2017, which are incorporated herein by reference in their entirety.

TECHNICAL FIELD

The present disclosure relates to the technical field of medical instruments, and in particular, to a device for introducing a new radioactive source and removing an old radioactive source in a radioactive source body of radiotherapy equipment.

BACKGROUND

Tumor is a common and frequently-occurring disease, and radiation therapy is a common treatment means for tumor. Radiation therapy equipment utilizes radioactive rays to penetrate through human tumors and kill tumor tissues to achieve a therapeutic purpose.

There are many ways to generate radioactive rays in existing radiotherapy equipment, one of which is to generate radioactive rays by radioactive nuclide decay, for example, using the decay of cobalt-60 to generate gamma rays. For radiotherapy equipment using radionuclides, in the prior art, before a radioactive source is installed, it is necessary to construct an operating room for shielding radioactive rays with shield blocks outside the radiotherapy equipment, and the operation room is commonly called a hot chamber. A lead canister for carrying a radioactive source and a pick-up device are placed in the hot chamber. A hanging basket provided with the radioactive source is lifted from the lead canister by a lifting device placed in a designated position of the hot chamber by outdoor control operated outside the hot chamber, and the radioactive source is loaded into the radiotherapy equipment by the pick-up device. After the loading work is finished, the hot chamber constructed by the shield blocks is removed.

Since the shield blocks for constructing the hot chamber are made of heavy metal materials, and a space to be constructed must accommodate the lead canister for carrying the radioactive source and the pick-up device, therefore, the construction and the removal of the hot chamber is time consuming, labor intensive and difficult to operate.

Moreover, after the radiotherapy equipment is used for a certain period of time, the radioactivity of the radioactive source thereof becomes weak due to decay. For example, a half-life of cobalt-60 is 5.27 years, and in order to ensure a dose rate thereof at the focus, the radioactive source needs to be replaced every 6 years or so. It is necessary to build a hot chamber again when replacing the radioactive source, and it is difficult to construct and remove the hot chamber.

In addition, if the radiotherapy equipment fans during use, especially in a case where the machine failure occurs on a treatment head, maintenance personnel need to enter the treatment room for maintenance. However, since the radioactive source cannot be easily removed, the radiotherapy equipment is easy to occur radiation leakage when the maintenance is performed by the maintenance personnel, which increases radiation risk for the maintenance personnel during maintenance.

SUMMARY

Some embodiments of the present disclosure provides a radioactive source removing and introducing tooling, a smart cart and a radioactive source removing and introducing system, and a source introducing and source removing of the radioactive source may be realized by means of a cooperation between the radioactive source removing and radioactive introducing tooling and the smart cart, thereby reducing labor intensity, labor costs and radiation risk of the radioactive source.

In order to solve the above technical problems, some embodiments of the present disclosure adopts the following technical solutions:

The present disclosure provides a radioactive source removing and introducing tooling, and the radioactive source removing and introducing tooling includes a first support frame; a shield door disposed on the first support frame, and the shield door includes a movable first shield block; a shield cover located above the shield door, the shield cover is able to separate from the shield door, and the shield cover includes a first opening and an accommodation space; a first pull rod device disposed on the shield cover, the first pull rod device includes a pull rod and a first connection portion disposed on the pull rod, and the pull rod is able to extend into the accommodation space of the shield cover and drive the first connection portion to move inside the accommodation space of the shield cover.

The present disclosure provides a smart cart, and the smart cart includes a movable second support frame and a shield box fixed on the second support frame.

The shield box includes a box body and a cover body, the box body includes an opening and an accommodation space, and the cover body is able to close or open the box body.

The present disclosure provides a radioactive source removing and introducing system, and the system includes the radioactive source removing and introducing tooling as described in any one of the present disclosure and the smart cart as described in any one of the present disclosure.

Some embodiments of the present disclosure provides a radioactive source removing and introducing tooling, a smart cart and a radioactive source removing and introducing system. A source storage tank is located below the first support frame, and by adjusting a position of the source storage tank, the shield door is located above the source storage tank and the shield cover is placed above the shield door. First, the first shield block moves to a position away from the opening of the source storage tank by movement of the first shield block to open the source storage tank, and by connecting the pull rod device disposed on the shield cover, which may be raised and lowered, and a connection portion disposed on a sealing member of the source storage tank, the pull rod drives the sealing member of the source storage tank to move, so that the sealing member of the source storage tank is located in the accommodation space of the shield cover. And then the first shield block is moved again so that the first shield block moves to a position of the opening of the source storage tank to close the source storage tank. Therefore, in a case where a radioactive source component is stored in the source storage tank, rays emitted from the radioactive source are prevented from leaking out during a separation of a tank body and the sealing member of the source storage tank. The radioactive source removing and introducing tooling provided by the present disclosure may open and close the source storage tank, and may prevent rays of the radioactive source component in the source storage tank from leaking out by remotely controlling the movement of the radioactive source removing and introducing tooling.

BRIEF DESCRIPTION OF THE DRAWINGS

In order to describe technical solutions in embodiments of the present disclosure or the prior art more clearly, the accompanying drawings to be used in the description of the embodiments or the prior art will be introduced briefly. Obviously, the accompanying drawings to be described below are merely some embodiments of the present disclosure, and a person of ordinary skill in the art can obtain other drawings according to these drawings without paying any creative effort.

DETAILED DESCRIPTION

The technical solutions of the present disclosure will be described in detail with reference to specific embodiments. Obviously, the described embodiments are merely some but not all of embodiments of the present disclosure. All other embodiments made on the basis of the embodiments of the present disclosure by a person of ordinary skill in the art without paying any creative effort shall be included in the protection scope of the present disclosure.

It should be noted that the radioactive source removing and introducing tooling and the smart cart provided by the present disclosure may be used cooperatively to realize the introduction and the removal of the radioactive source in the source storage tank, thereby eliminating the need for manual operation, and avoiding the risk of manual introduction and removal of a radioactive source. In the present disclosure, the radioactive source is generally a radioactive isotopic source, such as cobalt-60, which may emit radioactive gamma rays, thereby having a killing effect. The tank body of the source storage tank and the sealing member may be made of a shielding material, such as lead, tungsten, tungsten alloy, etc., which has a large shielding effect on rays, therefore, the radioactive source is placed in the source storage tank to facilitate transport of the radioactive source.

Figure 1:
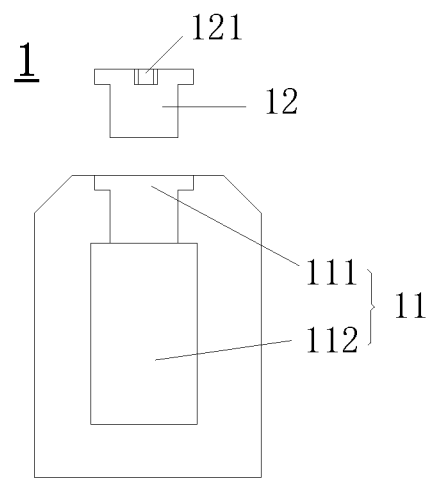
FIG. 1 is a schematic diagram of a source storage tank, according to some embodiments of the present disclosure.
Figure 2:
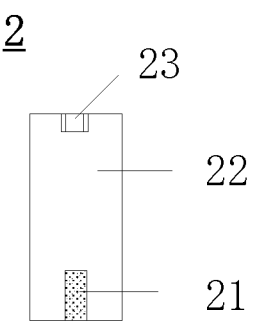
FIG. 2 is a schematic diagram of a radioactive source component, according to some embodiments of the present disclosure.

Generally, as shown in FIG. 1, a source storage tank 1 includes a tank body 11 and a sealing member 12; the tank body 11 includes an opening 111 and an accommodation space 112 for accommodating a radioactive source component; and the sealing member 12 is used for closing the opening 111. The source storage tank in the present disclosure may be used to store a radioactive source component 2, and as shown in FIG. 2, the radioactive source component 2 includes a radioactive source 21 and a carrier source body 22, and the radioactive source 21 is disposed on the carrier source body 22.

In the present application, as shown in FIG. 1, the sealing member 12 of the source storage tank is provided with a fourth connection portion 121. As shown in FIG. 2, the carrier source body 22 is provided with a third connection portion 23. The fourth connection portion is taken as an example, for example, the fourth connection portion may be an internal thread with a groove so as to be connected to other devices, and separate the sealing member of the source storage tank from the tank body by other devices. Of course, the specific structures of the third connection portion and the fourth connection portion are not limited in this disclosure. For example, the connection may be realized by electromagnetism, and the above example is merely used to exemplify the present disclosure.

An automatic radioactive source removing and introducing system provided by the present disclosure includes a radioactive source removing and introducing tooling and a smart cart, and the introduction and the removal of the radioactive source may be automatically realized by using the radioactive source removing and introducing tooling and the smart cart. For example, an old radioactive source component is removed from the radiotherapy equipment and stored in the source storage tank, and a new radioactive source component in another source storage tank is installed in the radiotherapy equipment. Therefore, radioactive source introducing, radioactive source removing and radioactive source replacing may be realized without the construction of a hot chamber and manual operation, which reduces radiation risk of an operator during an operation process of the radioactive source removal and introduction.

In the following, the radioactive source removing and introducing tooling and the smart cart in the present disclosure will be separately described, and then the automatic radioactive source removing and introducing system in the present disclosure will be exemplified with reference to specific embodiments.

Figure 3:
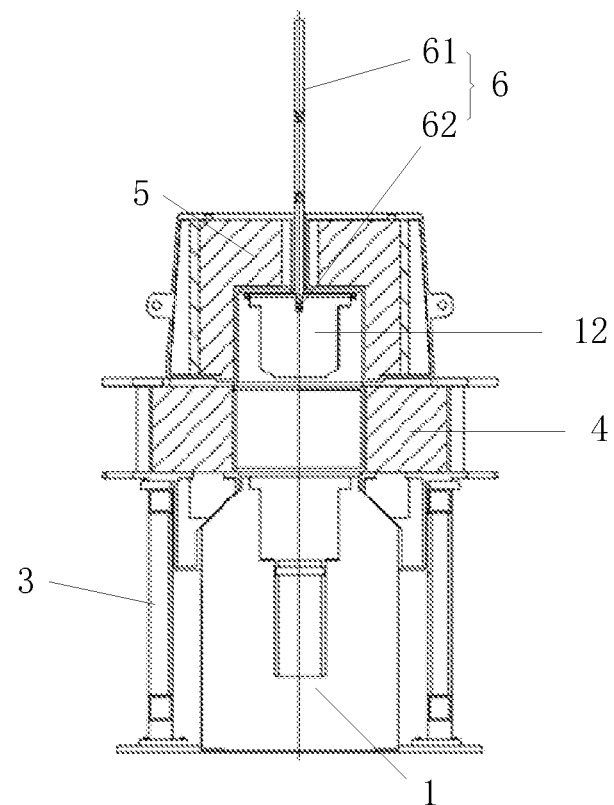
FIG. 3 is a schematic diagram of a source removing and introducing tooling, according to some embodiments of the present disclosure.
Figure 4:
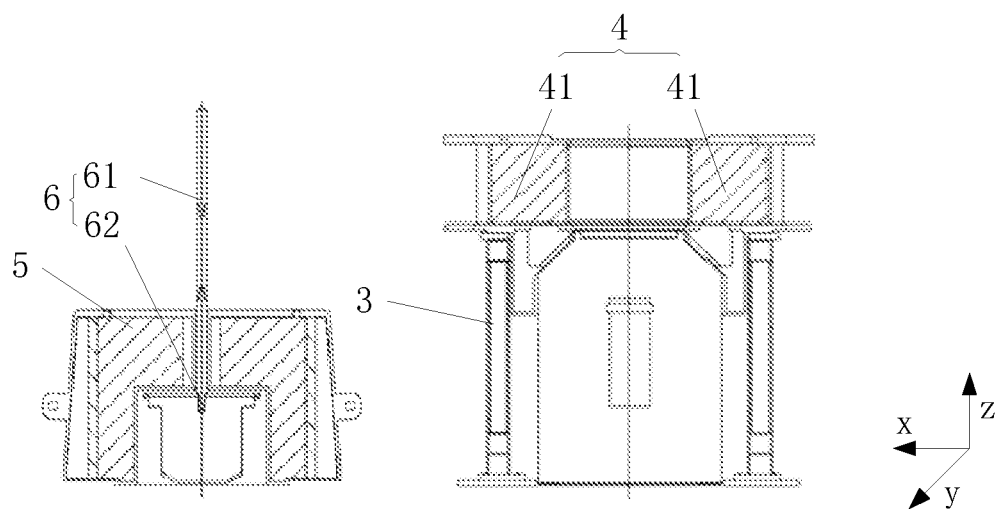
FIG. 4 is a split diagram of a source removing and introducing tooling, according to some embodiments of the present disclosure.

The radioactive source removing and introducing tooling provided by the present disclosure, as shown in FIG. 3 and FIG. 4, includes a first support frame 3, a shield door 4 disposed on the first support frame 3, a shield cover 5 located above the shield door 4, and a first pull rod device 6. The shield door 4 includes a movable first shield block 41. The shield cover 5 may be separated from the shield door 4, and the shield cover 5 includes a first opening 14 and an accommodation space. The first pull rod device 6 includes a pull rod 61 and a first connection portion 62 disposed on the pull rod 61, and the pull rod 61 may extend into the accommodation space of the shield cover 5 by the first opening 14 of the shield cover 5, and drive the first connection portion 62 to move inside the accommodation space of the shield cover 5. In the present disclosure, the first connection portion may be a part of the pull rod, or disposed on the pull rod device. For example, the first connection portion may be an external thread provided on the pull rod.

In the present disclosure, the first support frame plays a supporting role to support the shield door and the shield cover, so that the source storage tank may be located below the shield door. The specific structure of the first support frame is not limited, and the structure of the first support frame shown in FIG. 4 is only taken as an example for description. The shield door includes the movable first shield block. In FIG. 4, taking the shield door including two first shield blocks 41 as an example, the two first shield blocks 41 move along a direction 101, so that the opening of the source storage tank may be opened and closed. The shield door may also include only a single shield block, or two or more shield blocks. The number of shield blocks of the present application may be specifically set according to a specific structure of the source storage tank. For example, the shield door may include four first shield blocks, and the four first shield blocks are connected to each other to surround the opening of the source storage tank, and the opening of the source storage tank may be opened or closed by the movement of any one of the first shield block. Or the shield door may include a single first shield block, and the source storage tank may be opened or closed by the movement of the first shield block. And the movement of the first shield block may be driven by a motor or a gear. The specific structure and the driving mode of the shield door are not specifically limited in the present disclosure.

In addition, the shield cover 5 may be separated from the shield door 4, that is, the shield cover may be located above the shield door or removed from the shield door by manual operation or a lifting device. If other lifting devices are used, the movement of the shield cover may also realize an automatic remote operation.

For example, a spatial position structure of the accommodation space may also be set in cooperation with a structure of the radioactive source component. Of course, the accommodation space may also accommodate other radioactive objects, and the spatial position structure of the accommodation space may also be set according to shapes of other radioactive objects.

In the present disclosure, the movement of the first shield block, and the movement of the pull rod device may be achieved by the driving of a driver so as to be controlled remotely. The specific movement modes and structures may be implemented by referring to the existing motor driving a screw or motor driving a slide rail or an actuator driving a gear which is engaging with a ring, etc., which are not specifically limited in the present disclosure. For example, taking the first pull rod device as an example, the movement of the first pull rod device may be controlled automatically in an electronic and electrical mode, so that the first pull rod device may be raised and lowered automatically, thereby driving the first connection portion to move in the accommodation space of the shield cover. The first pull rod device is controlled to realize automatic motion, which may be completed by existing mechanical structures and drive controllers, etc., which is not specifically limited and illustrated in the present disclosure.

In the present disclosure, for example, the source storage tank is located below the first support frame, and the shield door is located above the source storage tank by adjusting a position of the source storage tank, and the shield cover is placed above the shield door. First, the first shield block moves to a position away from the opening of the source storage tank by the movement of the first shield block, thereby exposing the sealing member 12 of the source storage tank. The first pull rod device 6 disposed on the shield cover may be connected to a fourth connection portion 121 disposed on the sealing member 12 by the first connection portion 62, so that the sealing member is located in the accommodation space of the shield cover by the sealing member driving the pull rod to move. And then the first shield block is moved again so that the first shield block moves to a position of the opening of the source storage tank to close the source storage tank. Therefore, in a case where a radioactive source component is stored in the source storage tank, rays emitted from the radioactive source are prevented from leaking out during a separation of the tank body 11 and the sealing member 12 of the source storage tank. The radioactive source removing and introducing tooling provided by the present application may realize the opening and closing of the source storage tank and the raising and lowering of the pull rod, and may prevent rays of the radioactive source component in the source storage tank from leaking out by remotely controlling the movement of the radioactive source removing and introducing tooling.

In the radioactive source removing and introducing tooling provided by the present disclosure, the first support frame 3 may drive the shield door 4 disposed on the first support frame 3 and the shield cover 5 to move, that is, the first support frame 3 is a movable first support frame.

For example, a bottom of the first support frame is mounted with a roller, and movement of the first support frame is achieved by rolling of the roller. Or the bottom of the first support frame is mounted with a pulley to drive the first support frame to move along a predetermined guide rail. For example, the guide rail may be disposed on the ground, and the pulley may be embedded in the guide rail and move on the guide rail, so that the movement of the first support frame is achieved by movement of the pulley on the guide rail. For example, the pulley may be a slider. Of course, the movement of the first support frame along the guide rail may be realized by an electromagnetic guide rail. There are many modes for the first support frame to move. The mode for the movement of the first support frame is not specifically limited in the present disclosure. The above description is only taken as an example.

Generally, the movement of the first support frame may be completed by electric drive, and the electric drive may realize remote control of the movement of the first support frame. The specific drive mode may refer to the prior art, which will not be specifically described in the present disclosure.

In the radioactive source removing and introducing tooling provided by the present disclosure, the first support frame includes two planar support plates. Or the first support frame includes at least two support columns, for example, the first support frame includes three support columns or four support columns. If the first support frame includes two planar support plates, the source storage tank may be moved between the two support plates so as to be located below the first support frame. In the present disclosure, as shown in FIG. 3 and FIG. 4, the first support frame includes four support columns, and the source storage tank may move from a plurality of directions so as to be located below the first support frame.

The first support frame plays a role of supporting the shield door so that the source storage tank may be located below the shield door. In the present disclosure, as long as the source storage tank is located below the shield door, a supporting mode of the first support frame is not specifically limited in the present disclosure, and the above description is only taken as an example.

In the radioactive source removing and introducing tooling provided by the present disclosure, the shield door may be moved up and down relative to the first support frame. That is, a height of the shield door may be adjusted so that the source storage tanks with different heights may be used. For the movement of the shield door relative to the first support frame, for example, the first support frame includes a fixed bracket and a moving bracket, the fixed bracket and the moving bracket may be movably connected, and the shield door is disposed on the moving bracket, so as to achieve the movement of the shield door relative to the first support frame by the movement of the moving bracket relative to the fixed bracket. Or the first support frame is provided with a first movement mechanism, the shield door is provided with a second movement mechanism, and the first movement mechanism and the second movement mechanism may be connected movably and cooperatively. For example, the first movement mechanism may be a guide rail and the second movement mechanism may be a slider, so that a relative movement of the first support frame and the shield door is realized by driving the slider by a driver to move along the guide rail. It should be noted that the movement of the shield door may be realized in an electrical mode to remotely control the movement of the shield door.

Figure 5:
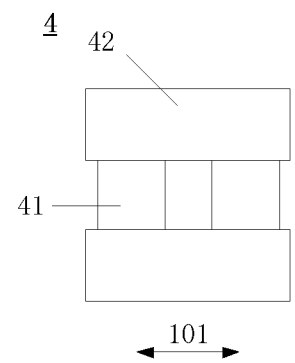
FIG. 5 is a schematic diagram of a shield door, according to some embodiments of the present disclosure.

The radioactive source removing and introducing tooling provided by the present disclosure is shown in FIG. 5, and the shield door further includes a second shield block 42 which is fixedly disposed, and the first shield block 41 is movable relative to the second shield block 42.

As shown in FIG. 5, the second shield block 42 is disposed on two opposite sides of the first shield block 41, and the first shield block 41 includes two sub-shield blocks. By providing the second shield block which is not movable, it is possible to further prevent leakage of rays during the movement of the first shield block. In the present disclosure, a specific structure of each shield block in the shield door may also be set according to a structure of the source storage tank, so as to increase a tightness of a connection between the source storage tank and the shield door.

Figure 6:
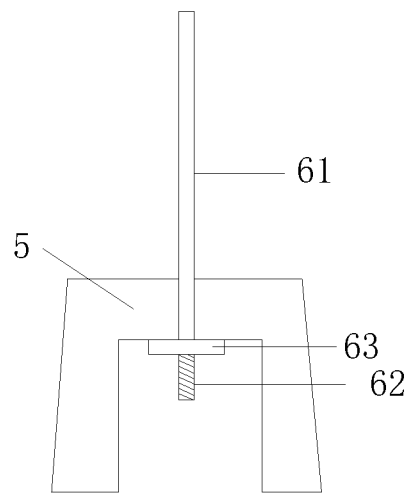
FIG. 6 is a schematic diagram of a shield cover, according to some embodiments of the present disclosure.

The radioactive source removing and introducing tooling provided by the present disclosure is shown in FIG. 6, and the shield cover 5 includes a side wall and a bottom connected to the side wall. The bottom is provided with a first through hole 13, and the pull rod 61 extends the first through hole 13 and protrudes from the bottom. Therefore, the pull rod may move in a straight line to drive the sealing member which is connected to the first connection portion to move.

In some embodiments, as shown in FIG. 3 and FIG. 4, the shield cover 5 further includes a lifting connector such as a lug, so that the shield cover is located above or removed from the shield door by connecting a lifting device and the lug.

The radioactive source removing and introducing tooling provided by the present disclosure is shown in FIG. 6, the pull rod 61 is provided with a limit block 63 on an end of the accommodation space of the shield cover 5. The limit block 63 is used to prevent the sealing member connected to the first connection portion 62 from shaking. On the other hand, a projection length of the limit block shown in FIG. 6 is greater than an aperture of the first through hole. Therefore, it is possible to further prevent the rays emitted from the radioactive source from leaking out of the first through hole.

The movement of the pull rod may also be achieved by electronic and electrical drive, for example, a motor drives rotation of the pull rod to achieve its movement, so that the movement of the pull rod may be controlled remotely. In addition, a connection between the first connection portion and the sealing member may also be realized by remote control, for example, the connection between the first connection portion and the sealing member is a threaded connection, so the connection between the first connection portion and the sealing member may be realized by the rotation of the pull rod which is driven by the motor. Of course, the first connection portion and the sealing member may also be connected by means of electromagnetism, so that the connection may also be achieved by remote control. The connection mode of the first connection portion and the sealing member is not specifically limited. The above description is only taken as an example.

Figure 7:
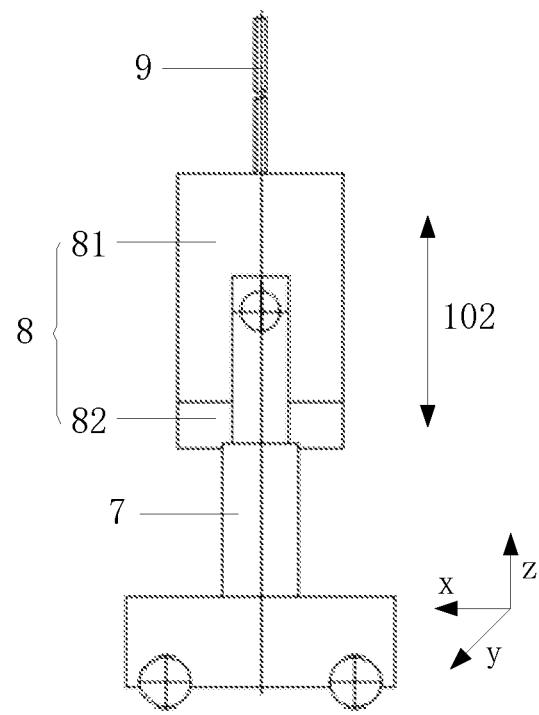
FIG. 7 is a schematic diagram of a smart cart, according to some embodiments of the present disclosure.

A smart cart provided by the present application is shown in FIG. 7, and the smart cart includes: a movable second support frame 7, a shield box 8 mounted on the second support frame 7, and a second pull rod device 9. The shield box 8 includes a box body 81 and a cover body 82, the box body 81 includes an opening and an accommodation space for accommodating the radioactive source component, and the cover body 82 may close and open the box body 81. The second pull rod device 9 includes a pull rod and a second connection portion (not shown in FIG. 7) disposed on the pull rod, and the pull rod may extend into the accommodation space of the shield box 8 and drive the second connection portion to move in the accommodation space of the shield box 8.

Referring to FIG. 7, the second support frame 7 is used to support the shield box 8 and the second pull rod device 9, so that the shield box may be located above the shield door of the radioactive source removing and introducing tooling. And the shield box 8 may also be communicated with the shield door of the radioactive source removing and introducing tooling. The shield door may be used to close the opening of the shield box. In a case where the shield door is open, the radioactive source component may be transferred between the shield box and the source storage tank located below the shield door, and the leakage of the rays emitted from the radioactive source component is prevented to ensure operation safety. In addition, the second support frame may also drive the shield box and the second pull rod device 9 to move in a plane where x and y are located. A specific structure of the second support frame is not limited in the present disclosure, and the specific structure of the second support frame shown in FIG. 6 is only taken as an example for description.

In the present disclosure, the second pull rod device of the smart cart may be the same as or different from the first pull rod device of the radioactive source removing and introducing tooling. In the following, a situation that the second pull rod device of the smart cart is the same as the first pull rod device of the radioactive source removing and introducing tooling is taken as an example for description. The second connection portion may also be an external thread, etc., so as to be connected to the third connection portion of the radioactive source component through threads. The pull rod may drive the radioactive source component to be located in the accommodation space of the box body, so that the cover body may close the radioactive source component in the shield box to prevent the rays emitted from the radioactive source from leaking out.

For example, the spatial position structure of the accommodation space may also be set in cooperation with the structure of the radioactive source component. Of course, the accommodation space may also accommodate other radioactive objects, or the spatial position structure of the accommodation space may also be set according to shapes of other radioactive objects.

In the smart cart provided by the present disclosure, a bottom of the second support frame is mounted with a roller, that is, the movement of the second support frame is realized by rolling of the roller. Or the bottom of the second support frame is mounted with a pulley to drive the second support frame to move along a predetermined guide rail. For example, the guide rail may be disposed on the ground, and the pulley may be embedded in the guide rail, and move on the guide rail, so that the movement of the second support frame is achieved by the movement of the pulley on the guide rail. Of course, there are many modes for the second support frame to move. The mode for the movement of the second support frame is not specifically limited in the present disclosure. The above description is only taken as an example. For example, the movement of the second support frame may be completed by electric drive, and the electric drive may realize remote control of the movement of the second support frame.

Figure 8:
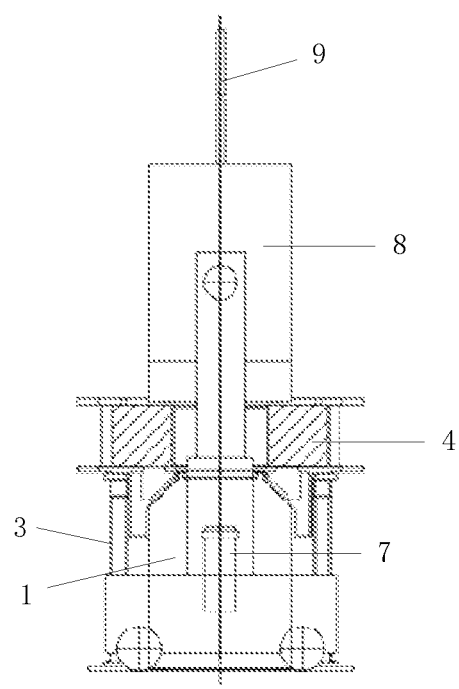
FIG. 8 is a schematic diagram showing a cooperation between a smart cart and a source removing and introducing tooling, according to some embodiments of the present disclosure.

The smart cart provided by the present disclosure is shown in FIG. 8, and the shield box 8 of the smart cart may be located above the shield door 4 of the radioactive source removing and introducing tooling. By opening the shield door 4, the second pull rod device 9 may extend into the source storage tank 1. Therefore, the radioactive source component may be taken out from the source storage tank 1 and accommodated in the shield box 8, and then the shield box 8 is closed. In this way, the radioactive source component may be removed by the smart cart and is installed in the radiotherapy equipment without manual operation, thereby avoiding radiation risk of manual operation.

Similarly, the radioactive source component may also be removed from the radiotherapy equipment by the smart cart, and is accommodated in the shield box 8. The shield box 8 and the shield door 4 are opened, so that the second pull rod device 9 may extend into the source storage tank 1, and the radioactive source component may be stored in the source storage tank 1, and then the shield door 4 is closed, and then the sealing member of the source storage tank 1 is installed at the opening of the source storage tank 1 by the shield cover 5 to close the source storage tank 1. In this way, the smart cart may realize the storage of the radioactive source component, and manual operation is reduced, thereby avoiding radiation risk of manual operation.

In the smart cart provided by the present application, the second support frame includes two planar support plates. Or the second support frame includes at least two support columns. For example, the second support frame includes three support columns or four support columns. Taking the second support frame including two planar support plates as an example, the radioactive source removing and introducing tooling may be located between the two support plates so that the shield box is located above the shield door. Of course, in a preferred solution, the second support frame includes four support columns.

The second support frame plays a supporting role, so that the shield box may be located above the shield door of the radioactive source removing and introducing tooling. In the present application, as long as the shield box is located above the shield door of the radioactive source removing and introducing tooling, a supporting mode of the second support frame is not specifically limited in the present disclosure, and the above description is only taken as an example.

In the smart cart provided by the present disclosure, the shield box may move up and down relative to the second support frame. That is, a height of the shield box may be adjusted. For the movement of the shield door relative to the second support frame, for example, the second support frame includes a fixed bracket and a moving bracket, the fixed bracket and the moving bracket are movably connected, and the shield box is disposed on the moving bracket, so as to achieve movement of the shield box relative to the second support frame by the movement of the moving bracket relative to the fixed bracket.

Or in the smart cart provided by the present disclosure, the second support frame is provided with a first motion mechanism, the shield box is provided with a second motion mechanism, and the first motion mechanism and the second motion mechanism are connected movably and cooperatively. For example, the first motion mechanism may be a guide rail, and the second motion mechanism may be a slider, so that a relative movement of the second support frame and the shield box is realized by the slide block and the guide rail. It should be noted that the movement of the shield box may be realized in an electrical mode so as to remotely control the movement of the shield box.

Figure 9:
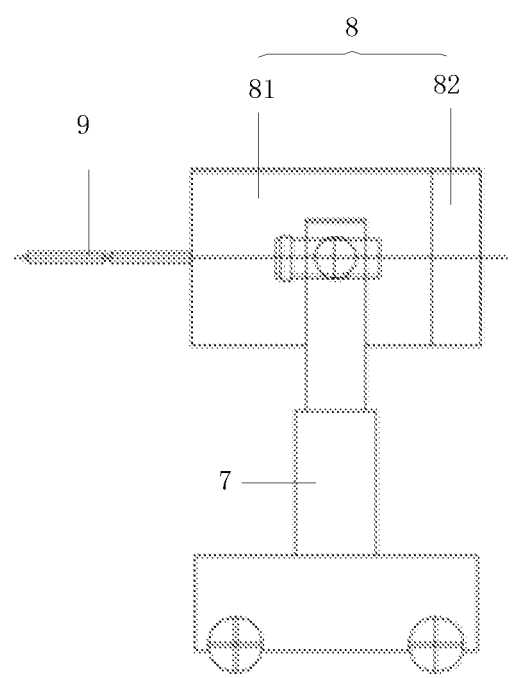
FIG. 9 is a schematic diagram of another smart cart, according to some embodiments of the present disclosure.

In the smart cart provided by the present disclosure, the shield box may be rotated relative to the second support frame. As shown in FIG. 9, an example that the shield box 8 is rotated by 90 degrees is given for description. Of course, the shield box may be rotated, and a rotation angle thereof may be set and adjusted as needed. The present disclosure does not limit the rotation angle of the shield box, for example, the shield box may be rotated by 180 degrees or 360 degrees.

In the smart cart provided by the present disclosure, for example, the shield box is mounted on the second support frame through a rotating shaft, so that the shield box is rotated around the rotating shaft. Of course, the rotation of the shield box and the second support frame may be implemented in various modes, which is not specifically limited in the present disclosure. For example, the shield box may also be rotated by a bearing gear or the like. It should be noted that the rotation of the shield box may be realized by remote control.

In the smart cart provided by the present disclosure, the second support frame may further include two parts that may move relative to each other. For example, the second support frame includes an upper bracket and a lower bracket, and the upper bracket and the lower bracket may move up and down relative to each other, or the upper bracket and the lower bracket may be connected rotatably, and if the shield box is fixed on the upper bracket, the rotation or movement of the shield box is also driven by the relative rotation or movement of the upper bracket and the lower bracket. The present disclosure does not specifically limit the structure of the smart cart and the motion mode of the shield box, and the above is only taken as an example for illustration.

In the smart cart provided by the present disclosure, the shield box includes a side wall and a bottom connected to the side wall, the bottom is provided with a second through hole 15, and the pull rod extends through the second through hole 15 and protrudes from the bottom, so that the pull rod may move in a straight line to drive the radioactive source component connected to the second connection portion to move.

In the smart cart provided by the present disclosure, the pull rod is provided with a limit block for preventing the radioactive source component connected to the second connection portion from shaking. In the smart cart provided by the present disclosure, referring to FIG. 6, the projection length of the limit block is greater than the aperture of the second through hole. Therefore, it is possible to further prevent the rays emitted from the radioactive source from leaking out of the second through hole.

In the smart cart provided by the present disclosure, the cover body is movably connected to the box body. For example, the cover body may be connected to the box body by a hinge, thus the cover body may be opened or closed. Or the cover body may be moved relative to the box body, that is, the cover body may be opened or closed by a push-pull movement. It should be noted that the movable connection or relative movement of the cover body and the box body may also be implemented by a driver so as to remotely control the movement of the shield box.

A radioactive source removing and introducing system provided by the present disclosure, includes the radioactive source removing and introducing tooling and the smart cart provided by the present disclosure. The removal and introduction of the radioactive source component in the radiotherapy equipment may be realized by the cooperation between the radioactive source removing and introducing tooling and the smart cart. Further, the shield box of the smart cart is communicated with the shield door of the radioactive source removing and introducing tooling, and the shield door may be used to close the shield box. And in a case where the shield door is opened, the radioactive source component may be transferred between the shield box and the source storage tank located below the shield door, and the leakage of the rays emitted from the radioactive source component is prevented to ensure operation safety.

For example, radioactive source replacing of the radiotherapy equipment is taken as an example, that is, the radiotherapy equipment is mounted with a radioactive source component, and the radioactive source component in the radiotherapy equipment needs to be replaced with a new radioactive source component after a certain period of use.

As shown in FIG. 3, the source storage tank 1 is placed below the shield door 4 of the radioactive source removing and introducing tooling, and the shield cover 5 is placed above the shield door 4 (of course, the radioactive source removing and introducing tooling may also be remotely controlled by the lifting device to be located above the source storage tank). The first shield block of the shield door 4 is controlled to move so as to form an opening on the shield door 4. The first connection portion above the pull rod 61 is connected to the fourth connection portion 121 of the sealing member 12 by controlling the first pull rod device 6, and the sealing member 12 is pulled into the accommodation space of the shield cover 5 by the pull rod 61. Further, the shield cover 5 may be separated from the shield door 4 by a lifting device.

By remotely controlling the movement of the smart cart, the smart cart is connected to the radiotherapy equipment, and the cover body of the shield box in the smart cart is opened. The second connection portion above the second pull rod device is connected to the third connection portion on the radioactive source component by controlling the second pull rod device, and the radioactive source component in the radiotherapy equipment is pulled into the accommodation space of the shield box by the pull rod, and then the cover body of the shield box is closed.

As shown in FIG. 8, the smart cart loaded with the radioactive source component is controlled to move to the position of the radioactive source removing and introducing tooling, and the shield box 8 may be located above the shield door 4 by adjusting the positions of the smart cart and the shield box. The first shield block of the shield door 4 is controlled to move so as to form an opening on the shield door 4. The cover body of the shield box 8 is opened, the radioactive source component is introduced into the source storage tank 1 by controlling the second pull rod device 9, and the second connection portion on the second pull rod device 9 is separated from the third connection portion 23 on the radioactive source component 2. In the present disclosure, the shield box of the smart cart is communicated with the shield door of the radioactive source removing and introducing tooling, and the shield door may be used to close the shield box. And in a case where the shield door is opened, the radioactive source component may be transferred between the shield box and the source storage tank located below the shield door, which may prevent the leakage of the rays emitted from the radioactive source component to ensure operation safety.

The first shield block of the shield door 4 of the radioactive source removing and introducing tooling is controlled to move so as to close the opening of the source storage tank 1 to prevent leakage of rays. The smart cart leaves the radioactive source removing and introducing tooling. Referring to FIG. 3, the shield cover 5 of the radioactive source removing and introducing tooling is repositioned above the shield door 4 of the radioactive source removing and introducing tooling, and then the first shield block is controlled to move so as to form an opening on the shield door 4. By controlling the first pull rod device 6, a sealing member is placed at the opening of the source storage tank 1 to close the opening of the source storage tank 1. Thus, a process of removing an old radioactive source is completed.

Similarly, as shown in FIG. 3, the radioactive source removing and introducing tooling is moved to the position of the source storage tank 1 with a new radioactive source component, and the shield door 4 is placed above the source storage tank 1. The shield block of the shield door 4 is controlled to move so as to form an opening on the shield door 4, and the first connection portion 62 above the first pull rod device 6 is connected to the fourth connection portion 121 of the sealing member 12 by controlling the first pull rod device 6, and the sealing member 12 is pulled into the accommodation space of the shield cover 5 by the pull rod 61. Finally, the first shield block of the shield door 4 is controlled to move so as to close the opening of the source storage tank 1 to prevent rays from being emitted.

As shown in FIG. 8, the smart cart is controlled to move to the position of the radioactive source removing and introducing tooling by remote control, and the shield box 8 may be located above the shield door 4 by adjusting the positions of the smart cart and the shield box. The first shield block of the shield door 4 is controlled to move so as to form an opening on the shield door 4, and the cover body of the shield box 8 is opened. The second connection portion above the second pull rod device 9 is connected to the third connection portion 23 of the radioactive source component 2 by controlling the second pull rod device 9, and the radioactive source component 2 is pulled into the accommodation space of the shield box 8 by the pull rod 9, and then the cover body of the shield box 8 is closed.

By remotely controlling the movement of the smart cart, the smart cart is connected to the radiotherapy equipment, the cover body of the shield box on the smart cart is opened, and the radioactive source component of the second pull rod device is placed into the radiotherapy equipment by controlling the second pull rod device.

The shield cover of the radioactive source removing and introducing tooling is repositioned above the shield door of the radioactive source removing and introducing tooling, and then the first shield block is controlled to move so as to form an opening on the shield door. By controlling the first pull rod device, the sealing member is placed at the opening of the source storage tank to close the opening of the source storage tank, thus an installation process of a new radioactive source is completed.

In the above process of removing and introducing the radioactive source body, both the radioactive source removing and introducing tooling and the smart cart may be remotely controlled to complete corresponding steps thereof. Therefore, labor intensity and labor cost, and radiation risk of radioactive source loading and removing may be reduced.

The automatic radioactive source removing and introducing system provided by the present disclosure may realize an automatic radioactive source introduction and removal by the smart cart and the radioactive source removing and introducing tooling, thereby eliminating the need for operators and avoiding radiation to the workers during the process of radioactive source introduction and removal. And even if the workers are needed, the source storage tank may be closed by enclosing the radioactive source component in the shield box of the smart cart, or by using the shield door of the radioactive source removing and introducing tooling, so as to avoid radiation leakage and endangering the safety of the workers.

Of course, the source storage tank may also be placed on a moving cart, or a moving device is disposed at the bottom of the source storage tank such as a pulley or the like, so that the source storage tank may be freely moved to facilitate a docking between the source storage tank and the radioactive source removing and introducing tooling more conveniently.

Further, a fixed motion track is set for the radioactive source removing and introducing tooling and the smart cart, and a plurality of source storage tanks are placed on the track, so that the movement of the radioactive source removing and introducing tooling and the smart cart may realize the docking more easily.

In the present disclosure, the radiotherapy equipment may further include two treatment heads, each treatment head is provided with one radioactive source component. The two treatment heads may be oppositely disposed to form a motion track connecting the two treatment heads between the two treatment heads. The smart cart, the radioactive source removing and introducing tooling, and the source storage tank may all be disposed on a path of the track, and the movement thereof along the track may realize position change between each other, thereby facilitating the docking, facilitating radioactive source removing, loading or replacing.

Another smart cart provided by the present disclosure includes a movable second support frame and a shield box fixed on the second support frame. The shield box includes a box body and a cover body, the box body includes an opening and an accommodation space, and the cover body may close or open the box body.

Thus, the smart cart is controlled to move to the position of the radioactive source removing and introducing tooling, and the shield box may be located above the shield door by adjusting the positions of the smart cart and the shield box. The first shield block of the shield door is controlled to move so as to form an opening on the shield door. The cover body of the shield box is opened, the radioactive source component is introduced into the source storage tank by controlling the second pull rod device, and the second connection portion on the second pull rod device is separated from the third connection portion on the radioactive source component. In the present disclosure, the shield box of the smart cart is communicated with the shield door of the radioactive source removing and introducing tooling, and the shield door may be used to close the shield box. And in a case where the shield door is opened, the radioactive source component may be transferred between the shield box and the source storage tank located below the shield door, which may prevent the rays emitted from the radioactive source component from leaking out and ensure operation safety.

In the embodiment, the shield box is detachably fixed on the second support frame. For example, the shield box and the second support frame are respectively provided with a connecting member. The shield box may be connected to the second support frame by the connecting members when needed, so that the shield box is fixed on the second support frame, and the shield box is driven to move by the second support frame. The second support frame may also be disconnected from the shield box when moved to a fixed position.

For example, the second support frame is provided with a fixing portion, and the shield box is provided with a fixing member, and the fixing portion is fixedly connected to the fixing member. For example, the fixing portion may be a groove, and the fixing member may be a rod member placed in the groove. Of course, the fixing portion and the fixing member may also be fixedly locked by other structures to prevent the fixing from being unstable.

In the embodiments provided by the present disclosure, the fixing member and the shield box are detachably fixed. For example, the shield box is provided with an internal thread, and the fixing member and the shield box may be fixed by threads. Of course, a fixed mode of the fixing member and the shield box is not limited in the present disclosure, and the above is only taken as an example for illustration.

Of course, the shield box may be rotated relative to the second support frame, or moved up and down relative to the second support frame. The specific structures of the shield box and the second support frame may be referred to the previous description, which will not be described here again.

A radioactive source removing and introducing system provided by the present disclosure, includes the radioactive source removing and introducing tooling and the smart cart provided by the present disclosure. The removal and introduction of the radioactive source component in the radiotherapy equipment may be realized by the cooperation between the radioactive source removing and introducing tooling and the smart cart.

Further, the shield box of the smart cart is communicated with the shield door of the radioactive source removing and introducing tooling, and the shield door may be used to close the shield box. And in a case where the shield door is opened, the radioactive source component may be transferred between the shield box and the source storage tank located below the shield door, and the leakage of the rays emitted from the radioactive source component is prevented to ensure operation safety.

For example, the radioactive source replacing of the radiotherapy equipment is taken as an example, that is, the radiotherapy equipment is mounted with a radioactive source component, and the radioactive source component in the radiotherapy equipment needs to be replaced with a new radioactive source component after a certain period of use.

A shield box is fixed in the radiotherapy equipment, and the radioactive source component of the radiotherapy equipment may move in the shield box. The radioactive source component of the radiotherapy equipment may be placed into the shield box when needed.

The smart cart moves to the vicinity of the radiotherapy equipment, so that the second support frame of the smart cart is fixed with the shield box, so that the smart cart may drive the shield box to move to other positions for further processing.

The smart cart further places the shield box into other shielding devices for shielding, or the radioactive source introduction and removal of the radioactive source component may be realized by cooperation between the smart cart and the radioactive source removing and introducing tooling.

For example, in the embodiment, the shield box is detachably fixed on the second support frame. For example, the shield box and the second support frame are respectively provided with a connecting member. The shield box may be connected to the second support frame by the connecting members when needed, so that the shield box is fixed on the second support frame, so that the shield box is driven to move by the second support frame. The second support frame may also be disconnected from the shield box when moved to a fixed position. In this case, the shield box is equivalent to the source storage tank in the embodiments of the present disclosure, and the source removing and introducing tooling may move to a corresponding position of the shield box to remove the radioactive source component in the shield box. The specific cooperation between the radioactive source removing and introducing tooling and the source storage tank to remove the radioactive source component may be referred to the above specific description for the cooperation between the radioactive source removing and introducing tooling and the source storage tank, which will not be described here again.

The shield box loaded with a new radioactive source component may be transferred and fixed to a fixed position in the radiotherapy equipment by the smart cart. The radiotherapy equipment cooperates with the shield box to allow the new radioactive source component to be assembled in the radiotherapy equipment.

Different from the above-mentioned radioactive source introduction and removal of the radiotherapy equipment, the implementation method does not need to remove the radioactive source component, but stores the radioactive source component in the shield box for transportation and radioactive source introduction and removal, thereby further reducing a risk of radioactive source introduction and removal of the radioactive source component.

In the description of the present disclosure, it should be understood that the orientation or positional relationship indicated by the terms "upper", "lower", "left", "right", "vertical", "horizontal", "top", "bottom", "inner", "outer" and so on is based on the orientation or positional relationship shown in the drawings, and is merely for the convenience of description of the present disclosure and simplification of the description, rather than indicating or implying that the device or the component must have a particular orientation, and must be constructed and operated in a particular orientation, and thus cannot be construed as the limitation of the present disclosure. Moreover, the terms "first" and "second" are only used for describing a purpose, and cannot be construed as indicating or implying relative importance or implicitly indicating the number of technical features indicated. Thus, the features defined with "first" and "second" may explicitly or implicitly include one or more of the features. In the description of the present disclosure, unless otherwise stated, "a plurality of" means two or more than two. In addition, the terms "comprise", "include", and any deformation thereof are intended to cover a non-exclusive inclusion.

In the description of the present disclosure, it will be noted that the terms "installation", "communication", "connection" should be understood broadly unless specified or defined otherwise, for example, a fixed connection, a detachable connection, or an integral connection; a mechanical or electrical connection; a direct connections or an indirect connection via intermediaries; an inner communications between two elements. The specific meanings of the above terms in the present disclosure can be understood by those ordinary skilled in the art according to specific situations.

The foregoing descriptions are merely some implementation manners of the present disclosure any equivalent structure or equivalent process transformation according to the contents of the specification and the drawings of the present disclosure, is directly or indirectly used in other related technical fields, which shall all be included in the patent protection scope of the present disclosure.

What is claimed is:

1. A radioactive source removing and introducing tooling, comprising:
   a first support frame;
   a shield door disposed on the first support frame, wherein the shield door includes a movable first shield block;
   a shield cover located above the shield door, wherein the shield cover is able to separate from the shield door, and the shield cover includes a first opening and an accommodation space; and
   a first pull rod device disposed on the shield cover, wherein the first pull rod device includes a pull rod and a first connection portion disposed on the pull rod, and the pull rod is able to extend into the accommodation space of the shield cover and drive the first connection portion to move inside the accommodation space of the shield cover.

2. The radioactive source removing and introducing tooling according to claim 1, wherein the first support frame is movable.

3. The radioactive source removing and introducing tooling according to claim 2, wherein a bottom of the first support frame is mounted with a roller; or the bottom of the first support frame is mounted with a pulley which is able to drive the first support frame to move along a predetermined guide rail.

4. The radioactive source removing and introducing tooling according to claim 1, wherein the shield door is able to be moved up and down relative to the first support frame.

5. The radioactive source removing and introducing tooling according to claim 1, wherein the shield door further includes a second shield block which is fixedly disposed, and the first shield block is movable relative to the second shield block.

6. The radioactive source removing and introducing tooling according to claim 5, wherein
   the first shield block includes two sub-shield blocks, and the two sub-shield blocks are arranged in parallel so that two ends of the two sub-shield blocks are flush; and
   the second shield block includes two sub-shield blocks, one sub-shield block of the second shield block is located on a side of one end of the two sub-shield blocks of the first shield block, and another sub-shield block of the second shield block is located on a side of another end of the two sub-shield blocks of the first shield block.

7. The radioactive source removing and introducing tooling according to claim 1, wherein the shield cover includes a side wall and a bottom connected to the side wall, the bottom is provided with a first through hole, and the pull rod extends through the first through hole and protrudes from the bottom.

8. The radioactive source removing and introducing tooling according to claim 7, wherein an end of the pull rod inside the accommodation space of the shield cover is provided with a limit block.

9. A radioactive source removing and introducing system, comprising:
the radioactive source removing and introducing tooling according to claim 1; and
a smart cart comprising:
a movable second support frame; and
a shield box fixed on the second support frame, wherein the shield box includes a box body and a cover body, the box body includes an opening and an accommodation space, and the cover body is able to close or open the box body.

10. The radioactive source removing and introducing system according to claim 9, wherein the shield box of the smart cart is able to be communicated with the shield door of the radioactive source removing and introducing tooling.

11. The radioactive source removing and introducing system according to claim 9, wherein the radioactive source removing and introducing tooling and the smart cart are able to move along a same path.

12. A smart cart, comprising:
a movable second support frame;
a shield box fixed on the second support frame, and
a second pull rod device, wherein
the shield box is rotatable relative to the second support frame; the shield box includes a box body and a cover body, the box body includes an opening and an accommodation space, and the cover body is able to close or open the box body; and
the second pull rod device includes a pull rod and a second connection portion disposed on the pull rod, and the pull rod is able to extend into the shield box and drive the second connection portion to move in the accommodation space of the shield box.

13. The smart cart according to claim 12, wherein the shield box is detachably fixed on the second support frame.

14. The smart cart according to claim 13, wherein the second support frame is provided with a fixing portion, the shield box is provided with a fixing member, and the fixing portion is fixedly connected to the fixing member.

15. The smart cart according to claim 14, wherein the fixing member and the shield box are detachably fixed together.

16. The smart cart according to claim 12, wherein a bottom of the second support frame is mounted with a roller; or
a bottom of the second support frame is mounted with a pulley, and the pulley is able to drive the second support frame to move along a predetermined guide rail.

17. The smart cart according to claim 12, wherein the shield box is able to be moved up and down relative to the second support frame.

18. The smart cart according to claim 12, wherein the cover body is able to be movably connected to the box body; or the cover body is able to be moved relative to the box body.

* * * * *